US010456756B2

(12) United States Patent
Schwartz et al.

(10) Patent No.: US 10,456,756 B2
(45) Date of Patent: Oct. 29, 2019

(54) SOLID CHEMISTRY ENCLOSURE WITH SAFETY LOCK FOR DISPENSING APPLICATIONS

(71) Applicant: Ecolab USA Inc., Saint Paul, MN (US)

(72) Inventors: Daniel Ronald Schwartz, Saint Paul, MN (US); Ryan Joseph Drake, Saint Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

(21) Appl. No.: 16/100,896

(22) Filed: Aug. 10, 2018

(65) Prior Publication Data

US 2019/0046935 A1 Feb. 14, 2019

Related U.S. Application Data

(60) Provisional application No. 62/544,413, filed on Aug. 11, 2017.

(51) Int. Cl.
*B01D 11/02* (2006.01)
*A61L 2/00* (2006.01)
(Continued)

(52) U.S. Cl.
CPC .......... *B01F 1/0038* (2013.01); *B01F 1/0027* (2013.01); *B01F 1/0033* (2013.01);
(Continued)

(58) Field of Classification Search
CPC . A47L 240/00; A61K 8/00; A61L 2/00; A61L 2/0082; A61L 2/23; B67D 3/00
(Continued)

(56) References Cited

U.S. PATENT DOCUMENTS 3,864,090 A 2/1975 Richards
4,398,669 A 8/1983 Fienhold
(Continued)

FOREIGN PATENT DOCUMENTS

DE 4336339 A1 4/1995
EP 0225859 B1 6/1987
(Continued)

OTHER PUBLICATIONS

Ecolab USA Inc., PCT/US2018/046252 filed Aug. 10, 2018, "The International Search Report and the Written Opinion of the International Searching Authority, or the Declaration", 16 pages, dated Nov. 15, 2018.

(Continued)

*Primary Examiner* — Monzer R Chorbaji
(74) *Attorney, Agent, or Firm* — McKee, Voorhees & Sease, PLC

(57) ABSTRACT

A method and apparatus for obtaining a product chemistry from a slid block of caustic material is provided. The product is housed within a capsule which is positioned inside a turbulent flow dispenser, which utilizes fluid to erode the block and produce a concentrated solution. The fluid characteristics can be adjusted in the field to achieve a predetermined concentrate level of the solution. The capsule provides a safe and convenient means for handling, storing and shipping the caustic block without exposing the operator or handler to the hazardous material. The capsule includes nested components which can be rotated between a closed or sealed position and an open use position.

18 Claims, 9 Drawing Sheets

(51) Int. Cl.

| | |
|---|---|
| ***B08B 7/00*** | (2006.01) |
| ***B08B 3/00*** | (2006.01) |
| ***G07F 11/72*** | (2006.01) |
| ***B65D 83/00*** | (2006.01) |
| ***B01F 1/00*** | (2006.01) |
| ***B01F 15/00*** | (2006.01) |
| ***B01F 15/02*** | (2006.01) |
| *B01F 15/04* | (2006.01) |
| *B08B 3/08* | (2006.01) |

(52) U.S. Cl.
CPC .... *B01F 15/00253* (2013.01); *B01F 15/0203* (2013.01); *B01F 15/0416* (2013.01); *B01F 2001/0061* (2013.01); *B01F 2001/0077* (2013.01); *B08B 3/08* (2013.01)

(58) Field of Classification Search
USPC ....... 422/261, 264, 269, 274, 292, 300, 311, 422/902; 134/6, 138, 198; 221/30, 66
See application file for complete search history.

(56) References Cited

U.S. PATENT DOCUMENTS

| | | | |
|---|---|---|---|
| 4,643,881 | A | 2/1987 | Alexander et al. |
| 4,790,981 | A | 12/1988 | Mayer et al. |
| 5,089,127 | A | 2/1992 | Junker et al. |
| 5,133,381 | A | 7/1992 | Wood et al. |
| 5,389,344 | A | 2/1995 | Copeland et al. |
| 5,427,748 | A | 6/1995 | Wiedrich et al. |
| 5,441,073 | A | 8/1995 | Hoadley |
| 5,494,644 | A | 2/1996 | Thomas et al. |
| 5,505,915 | A | 4/1996 | Copeland et al. |
| 5,810,043 | A | 9/1998 | Grenier |
| 5,878,781 | A | 3/1999 | Parker |
| 5,897,770 | A | 4/1999 | Hatch |
| 5,928,608 | A | 7/1999 | Levesque et al. |
| 6,423,280 | B1 | 7/2002 | Tarara et al. |
| 7,325,747 | B2 | 2/2008 | Jonte |
| 7,597,861 | B2 | 10/2009 | Thomas et al. |
| 7,913,926 | B2 | 3/2011 | Goncze |
| 7,922,982 | B1 | 4/2011 | Brennan |
| 7,988,065 | B2 | 8/2011 | Spinelli et al. |
| 8,945,476 | B2 | 2/2015 | Carroll et al. |
| 9,643,143 | B2 | 5/2017 | Schultz et al. |
| 2005/0201200 | A1 | 9/2005 | Fleig |
| 2005/0244315 | A1 | 11/2005 | Greaves et al. |
| 2005/0258258 | A1 | 11/2005 | Jonte |
| 2006/0083668 | A1 | 4/2006 | Thomas |
| 2006/0231683 | A1 | 10/2006 | Orr |
| 2007/0253876 | A1 | 11/2007 | Limback et al. |
| 2012/0260997 | A1 | 10/2012 | Snetting et al. |
| 2012/0273585 | A1 | 11/2012 | Broome |
| 2014/0110352 | A1 * | 4/2014 | King ....................... C02F 1/688 210/754 |

FOREIGN PATENT DOCUMENTS

| | | | |
|---|---|---|---|
| EP | 0555600 | A1 | 2/1992 |
| EP | 1157230 | B1 | 5/2006 |
| EP | 2169511 | A1 | 3/2010 |
| FR | 2714044 | A1 | 12/1993 |
| GB | 2467064 | A | 7/2010 |
| WO | 2010027625 | A1 | 3/2010 |

OTHER PUBLICATIONS

Ecolab USA Inc. et al., PCT/US2013/026892 filed Feb. 20, 2013, Notification of Transmittal of the International Search Report and the Written Opinion of the International Searching Authority, or the Declaration, dated Jul. 23, 2013.

Ecolab USA Inc., PCT/US2014/016978 filed Feb. 18, 2014, "The International Search Report and the Written Opinion of the International Searching Authority, or the Declaration", dated Jun. 19, 2014.

Ecolab USA Inc, Application No. 14754429.0/PCT/US2014/016978, "Extended European Search Report" 8 pages, dated Nov. 29, 2016.

European Patent Office, "Extended European Search Report", issued in connection with International Application PCT/US2013026892, 7 pages, dated Oct. 7, 2015.

* cited by examiner

SOLID CHEMISTRY ENCLOSURE WITH SAFETY LOCK FOR DISPENSING APPLICATIONS

CROSS REFERENCE TO RELATED APPLICATIONS

This application claims priority under 35 U.S.C. § 119 to provisional application U.S. Ser. No. 62/544,413, filed Aug. 11, 2017. The provisional patent application is herein incorporated by reference in its entirety, including without limitation, the specification, claims, and abstract, as well as any figures, tables, appendices, or drawings thereof.

FIELD OF THE INVENTION

The present invention relates generally to a dispenser and method of operation for dispensing a solution from a solid chemistry product, which may be a caustic material formulation. More particularly, but not exclusively, the invention relates to a method and apparatus for safely and easily dissolving or eroding the solid product.

BACKGROUND OF THE INVENTIONS

Dissolution parameters of a solid product into a liquid solution, such as a liquid detergent used for cleaning and sanitizing, change based on the operating parameters of and inputs to the dissolution process. Spraying liquid onto a solid product to dissolve it into a liquid solution is one technique. With this technique, the operating parameters change in part based on characteristics within the dispenser, such as the distance between the solid product and the spray nozzle and the change in the pressure and temperature of the liquid being sprayed onto the solid product. Changes in a nozzle's flow rate, spray pattern, spray angle, and nozzle flow can also affect operating parameters, thereby affecting the chemistry, effectiveness, and efficiency of the concentration of the resulting liquid solution. In addition, dissolution of a solid product by spraying generally requires additional space within the dispenser for the nozzles spray pattern to develop and the basin to collect the dissolved product, which results in a larger dispenser.

Dispensing systems using turbulent flow technology have recently begun utilizing harder solid chemical blocks, which result in low concentration capabilities inside the dispenser. With turbulent flow technology, there are various adjustment options to control the solution concentration that exits the dispenser, such as submersion depth, puck-to-product height, the number of perforations in a manifold diffuser, the hole or slot size, the hole or slot layout, the water temperature, the water pressure, and the like. But there is a limit to these adjustment levels. For example, the perforations in the diffuser can only be made to a minimum diameter before fowling with dried chemistry over the life of the dispenser. Also, there is a minimum number of perforations required to fully cover the solid chemical blocks' surface to achieve even erosion. The turbulent flow technology platform has been moving toward more challenging solid blocks, including those made of caustic on hazardous material. As these blocks have become more and more difficult to handle and dispense, the bounds of safety have become an important factor.

Capsules are well-known for use in packaging solid chemistries. However, capsules incur added cost of packaging and processing time, as compared to plastic shrink-wrap pressed chemistries. However, capsules or other types of bottles and storage containers provide safety advantages, particularly for use with hazardous solid chemistries. For example, the capsule is typically sealed with a cap and/or shrink wrap to ensure that no chemistry leaks out during transit. Also, the capsule normally is stored and transported with a cap on top, to further aid in containing all of the chemistry. In use, the capsule is inverted before installation into a turbulent flow dispenser to allow a spray nozzle to introduce water or liquid upwardly into the capsule to erode the solid chemistry and thereby produce a concentrated solution. The installation process can expose the user to the chemistry, since the cap must be removed, thereby allowing powder or solid material inside the capsule to escape and potentially injure or harm the user.

Therefore, a need exists in the art for a method and apparatus for utilizing the turbulent flow technology to safely produce a solution concentration from a caustic solid chemistry product without risk to the operator.

BRIEF SUMMARY OF THE INVENTION

Accordingly, it is a principle object, feature and/or advantage of the present invention to provide an apparatus and method which improves on and/or overcomes the deficiencies of the prior art.

It is another object, feature and/or advantage of the present invention to provide a turbulent flow technology method and apparatus which utilizes a fluid to erode a solid chemistry block made of caustic material, and thereby create a solution with a desired concentration for dispensement.

It is a further object, feature and/or advantage of the present invention to provide a method and apparatus which allows for safe handling of caustic material in turbulent flow technology.

The solid chemistry capsule of the present invention is intended for use with turbulent flow technology so as to allow safe handling and usage of hazardous chemistries, such as pressed caustics. The capsule requires less package height than spray nozzles, as it does not require a full spray cone to be developed, thus eliminating user exposure to concentrated chemistry, while saving or minimizing storage space and shipping costs due to the shape and size of the capsule.

It is a further object, feature and/or advantage of the present invention to provide a method and apparatus that is usable across a wide variety of applications.

It is a further object, feature and/or advantage of the present invention to provide a method and apparatus which is cost effective.

It is a further object, feature and/or advantage of the present invention to provide an apparatus which is reliable, durable, and has a long useful life.

It is a further object, feature and/or advantage of the present invention to provide an apparatus that can be easily manufactured, installed, repaired, disassembled, stored, and cleaned.

It is a further object, feature and/or advantage of the present invention to provide an apparatus that is aesthetically pleasing.

The following provides a list of aspects and/or embodiments disclosed herein and are not to be limiting on the overall disclosure. It is contemplated that any of the embodiments disclosed herein can be combined with other embodiments, either in full or partially, as would be understood from a reading of the disclosure.

According to some aspects of the disclosure, a capsule for storing caustic solid product to be dissolved and dispensed by a turbulent flow dispenser includes an upper housing and a lower base coupled together to form a chamber for holding the caustic solid product and a pan inside the chamber and having perforations. The lower base also has perforations. The upper housing and lower base are rotatable relative to one another between a closed position wherein the perforations of the pan are misaligned with the perforations of the lower base and an open position wherein the perforations of the pan are aligned with the perforations of the lower base. The coupled upper housing and lower base are configured to fit inside a cavity in the dispenser wherein the product is dissolved to produce a solution.

According to additional aspects of the disclosure, the upper housing and the lower base are coupled together to form a cylindrical body.

According to additional aspects of the disclosure, the cylindrical body has a longitudinal axis, and rotation between the open and closed positions is about the longitudinal axis.

According to additional aspects of the disclosure, the upper housing and lower base are twist locked together.

According to additional aspects of the disclosure, one of the upper housing and lower base has a perimeter flange and the other of the upper housing and lower base has resilient fingers to releasably engage the flange so as to secure the upper housing and lower base together.

According to additional aspects of the disclosure, one of the upper housing and lower base has a lock button to prevent inadvertent rotation to the open positions.

According to additional aspects of the disclosure, one of the upper housing and lower base includes a key slot to mating receive a key tab in the dispenser to orient the housings in the cavity.

According to additional aspects of the disclosure, the perforations of the pan and the lower base are holes or slots.

According to additional aspects of the disclosure, the perforations of the pan are symmetrically positioned on a surface of the pan.

According to additional aspects of the disclosure, the perforations of the lower base are symmetrically positioned on a surface of the lower base.

According to additional aspects of the disclosure, the perforations of the pan are asymmetrically positioned with respect to every axis on a surface of the pan.

According to additional aspects of the disclosure, the perforations of the lower base are asymmetrically positioned with respect to every axis on a surface of the lower base.

According to additional aspects of the disclosure, the pan includes a sidewall which fits within a sidewall of the upper housing.

According to additional aspects of the disclosure, the lower base includes a sidewall which extends around a sidewall of the upper housing.

According to other aspects of the disclosure, a turbulent flow dispenser for producing a solution from a solid chemistry product includes a housing with a cavity therein, and with a perforated shelf in the cavity, a capsule configured to fit into the cavity and containing the solid chemistry product, and a fluid conduit for introducing fluid into the cavity when the capsule is in an open position. The capsule includes upper and lower members which are rotatable relative to one another between open and closed positions and has perforations which align with the shelf perforations when the capsule is in the open position and which are offset from the shelf perforations when the capsule is in the closed position.

According to additional aspects of the disclosure, the upper and lower members are separable for loading the solid chemistry product into the capsule.

According to additional aspects of the disclosure, the shelf supports the capsule in the cavity.

According to additional aspects of the disclosure, the shelf and lower member are keyed together in the cavity to allow rotation of the upper member relative to the lower member.

According to additional aspects of the disclosure, the shelf and the lower member integrally form one solid component.

According to additional aspects of the disclosure, the turbulent flow dispenser is free from a spray nozzle.

According to other aspects of the disclosure, a method for obtaining a product chemistry from a hazardous solid product includes providing a sealed capsule containing the hazardous solid product, installing the sealed capsule into a cavity in a turbulent flow dispenser, rotating a portion of the capsule to open perforations in the capsule, and introducing fluid through the capsule perforations to erode the solid product and produce a solution from the solid product and the fluid.

According to additional aspects of the disclosure, the capsule has an upper housing and a lower base which are rotatable relative to one another, and the rotation step rotates one of the upper and lower portions.

According to additional aspects of the disclosure, the upper housing and lower base are nested in a co-axial configuration, and the rotation is about a longitudinal axis of the nested portions.

According to additional aspects of the disclosure, the rotation step occurs after the capsule is installed in the cavity.

According to additional aspects of the disclosure, the rotation step occurs before the capsule is installed in the cavity.

According to additional aspects of the disclosure, the perforations are beneath the solid product in the capsule.

According to additional aspects of the disclosure, the method further includes locking the rotatable portion of the capsule against accidental rotation.

According to additional aspects of the disclosure, the capsule is cylindrical, and the rotation is about a longitudinal axis of the capsule.

According to additional aspects of the disclosure, an operator handles the capsule without exposure to the hazardous solid product.

These and/or other objectives, features, and advantages of the present invention will be apparent to those skilled in the art from the following detailed description of the illustrated embodiments, accompanied by the attached drawings wherein identical reference numerals will be used for like parts in the various views. The present invention is not limited to or by these objectives, features and advantages. No single embodiment need provide each and every objective, feature, or advantage.

Figure 1:
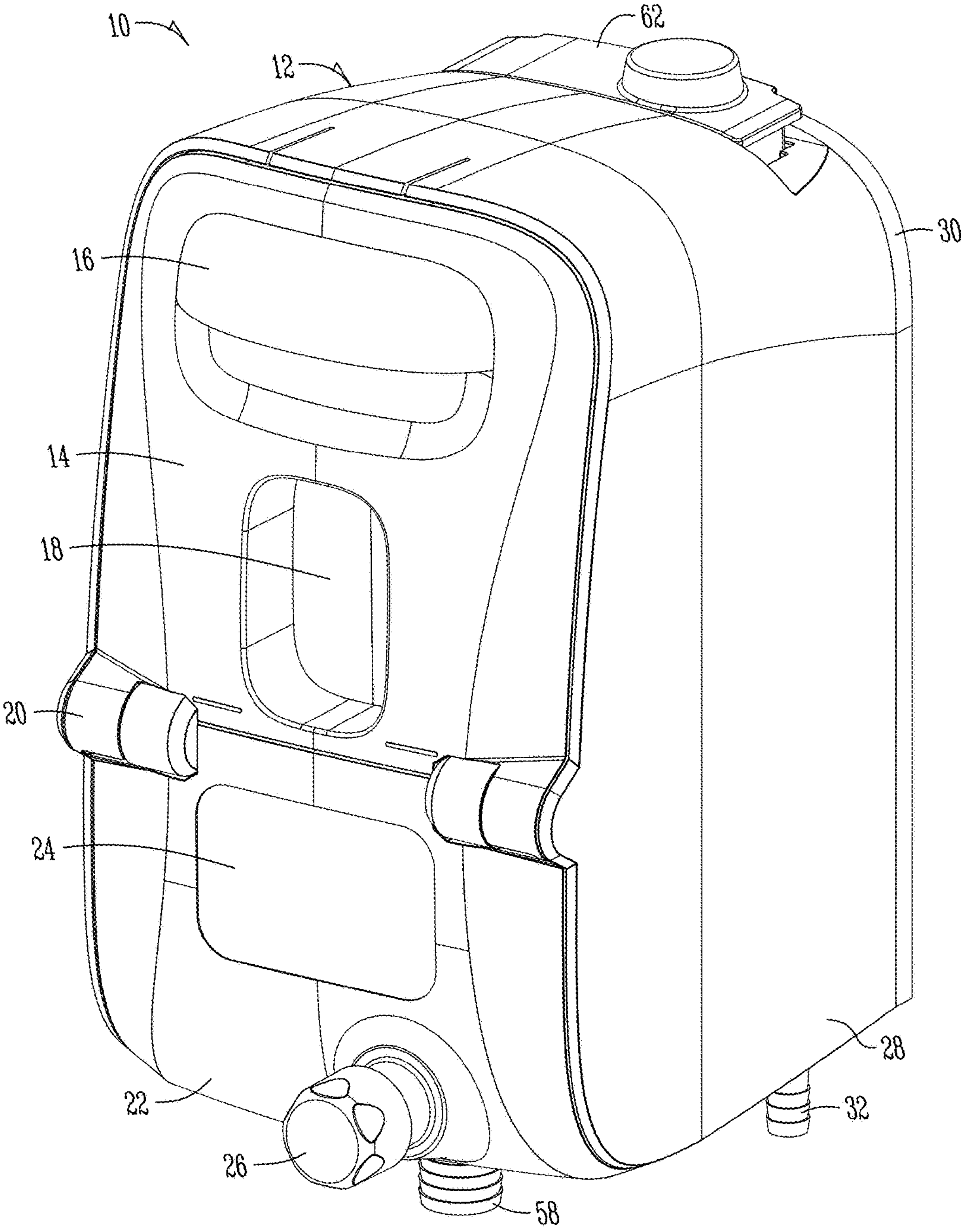
FIG. 1 is a perspective view of one embodiment of a turbulent flow technology dispenser according to the present invention.
Figure 2:
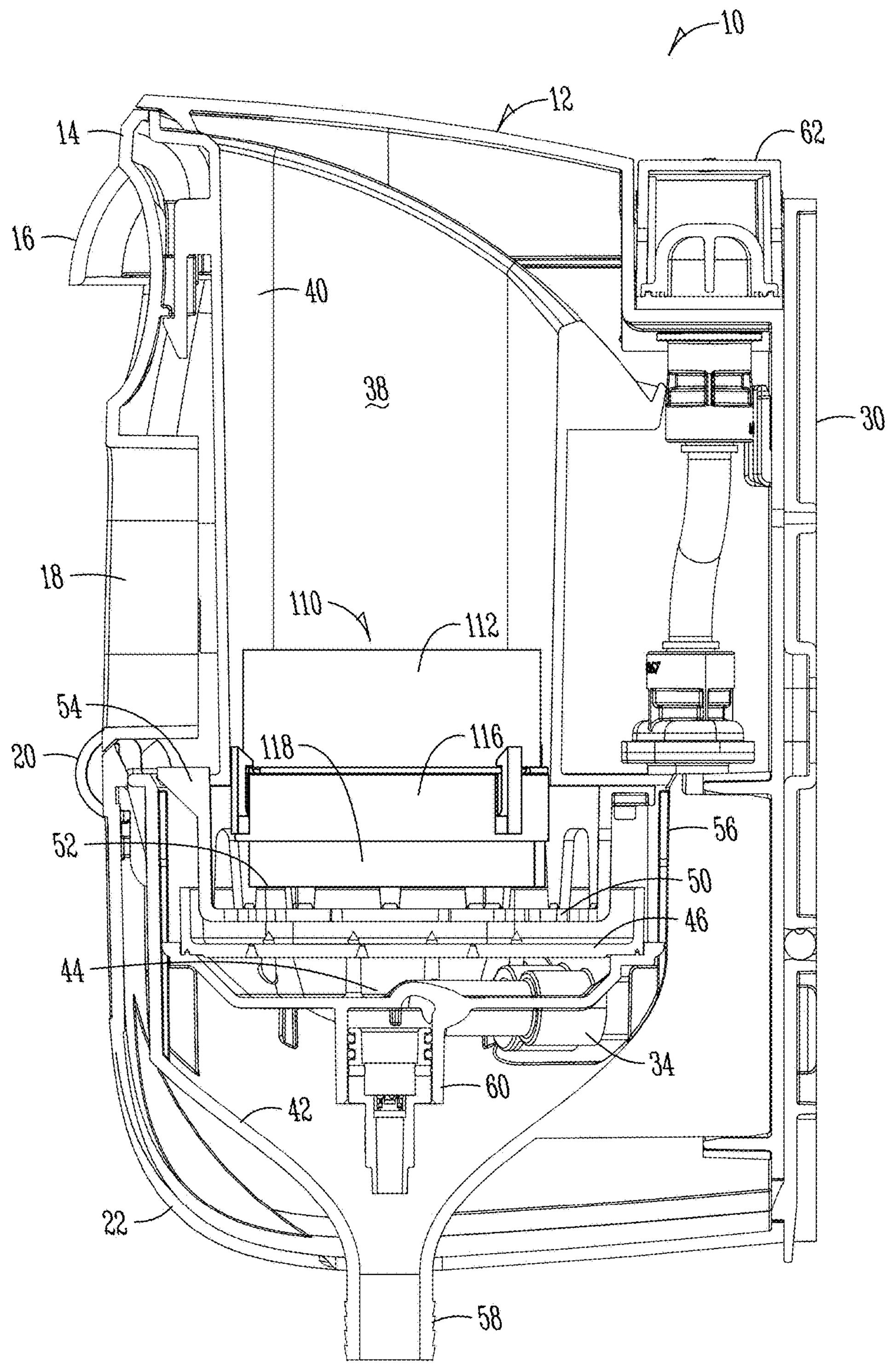
FIG. 2 is a sectional view of the dispenser, to show some of the internal components of the dispenser, including a caustic product capsule, in accordance with the present invention.
Figure 3:
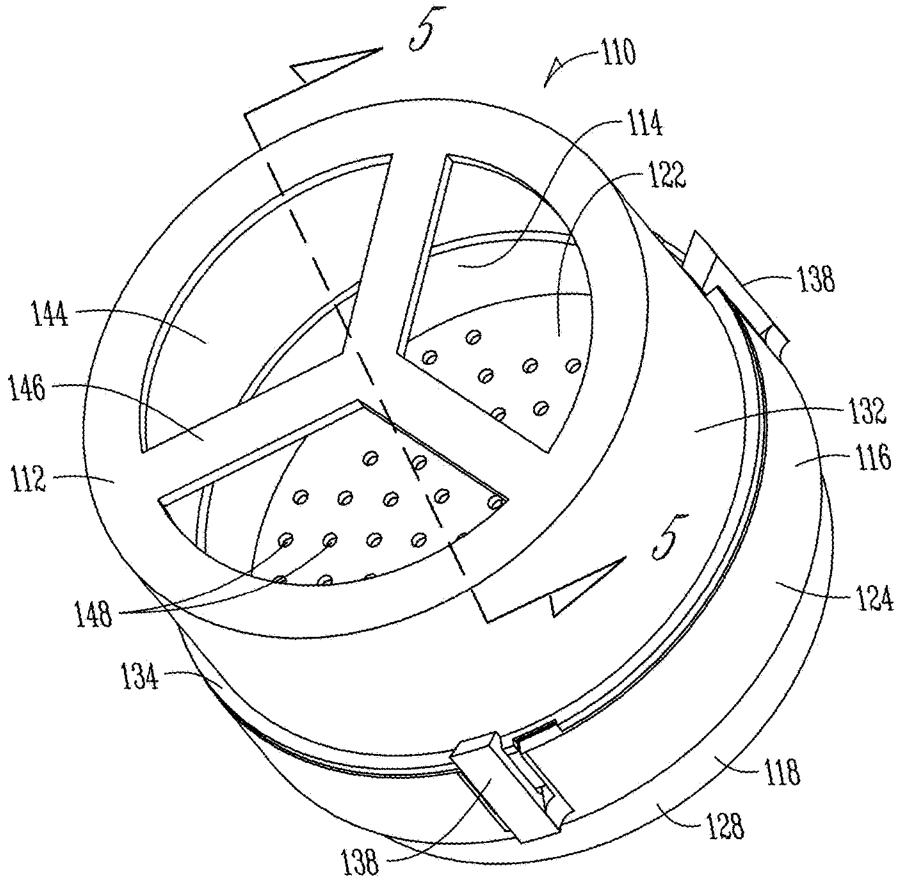
FIG. 3 is a perspective view of the capsule for containing caustic or hazardous solid material for use in the dispenser of FIG. 1.

Various embodiments of the present disclosure will be described in detail with reference to the drawings, wherein like reference numerals represent like parts throughout the several views. Reference to various embodiments does not limit the scope of the disclosure. Figures represented herein are not limitations to the various embodiments according to the disclosure and are presented for exemplary illustration of the disclosure.

DETAILED DESCRIPTION OF THE INVENTION

FIG. 1 shows an exemplary embodiment of a dispenser 10 for use with the present invention. However, it should be noted that other types and configurations of dispenser may be used with the invention, and the description and figures of the dispenser 10 are not to be limiting. The dispenser 10 is configured to hold a solid product chemistry that is combined with a fluid, such as water, alone, or a combination of water and air, to create a product chemistry solution. For example, the solid product chemistry may be mixed with fluid to create a cleaning detergent solution.

According to some embodiments, the dispenser 10 works by having the liquid, alone or with a gas, interact with the solid product to form a product chemistry having a desired concentration for its end use application. The liquid may be introduced to a bottom or other surface of the solid product, as will be discussed below.

Therefore, the dispenser 10 of the invention includes a novel turbulence or flow scheme control that is adjustable either manually or in real time (i.e., automatically) based on a characteristic of either the solid product or another uncontrolled condition, such as an environmental condition. The characteristic may be the density of the solid product, the temperature or pressure of the liquid, the climate (humidity, temperature, pressure, etc.) of the room in which the dispenser or solid product is placed, the type of liquid fluid used, the number of solid products used, or some combination thereof. The dispenser 10 can be adjusted, such as adjusting a characteristic of the existing flow scheme or turbulence. The adjustments may be made based upon the use of known relationships between the characteristic and the erosion rate of the solid product, as well as the relationship between different types of turbulence and the erosion rate of the solid product.

As mentioned, the turbulence or flow characteristics/scheme can be adjusted based upon known relationships between the characteristic(s) and the dispense rate of the solid chemistry. For example, by understanding the rate change of product dispense per change in degree of liquid temperature change, the turbulence can be adjusted to counteract a temperature change. The concentration is adjusted according to known relationships between the erosion or dispense rate and either the characteristic or the turbulence.

According to the exemplary embodiment, the dispenser 10 of FIG. 1 includes housing 12 comprising a front door 14 having a handle 16 thereon. The front door 14 is hingeably connected to a front fascia 22 via hinges 20 there between. This allows the front door 14 to be rotated about the hinge 20 to allow access into the housing 12 of the dispenser 10. The front door 14 also includes a window 18 therein to allow an operator to view the solid product housed with the housing 12. Once the housed product has been viewed to erode to a certain extent, the front door 14 can be opened via the handle to allow an operator to replace the solid product with a new un-eroded product.

The front fascia 22 may include a product ID window 24 for placing a product ID label thereon. The product ID window 24 allows an operator to quickly determine the type of product housed within the housing 12 such that replacement thereof is quick and efficient. The ID label may also include other information, such as health risks, manufacturing information, date of last replacement, or the like. The dispenser may be activated in various ways, such as a button, a switch, or a touch sensitive pad. For example, in one embodiment, a push button 26 is mounted to the front fascia 22 for activating the dispenser 10. The button 26 may be a spring-loaded button such that pressing or depressing of the button activates the dispenser 10 to discharge an amount of product chemistry solution via an outlet 58 created by the solid product and the liquid. Thus, the button 26 may be preprogrammed to dispense a desired amount per pressing of the button or may continue to discharge an amount of product chemistry while the button is depressed.

Connected to the front fascia 22 is a rear enclosure 28, which generally covers the top, sides, and rear of the dispenser 10. The rear enclosure 28 may also be removed to access the interior of the dispenser 10. A mounting plate 30 is positioned at the rear of the dispenser 10 and includes means for mounting the dispenser to a wall or other structure. For example, the dispenser 10 may be attached to a wall via screws, hooks, or other hanging means attached to the mounting plate 30.

The components of the housing 12 of the dispenser 10 may be molded plastic or other materials, and the window 18 may be a transparent plastic such as clarified polypropylene or the like. The handle 16 can be connected and disconnected from the front door 14. In addition, a backflow prevention device 62 may be positioned at or within the rear enclosure 28 to prevent backflow of the product chemistry.

A solid product is placed within a cavity 38, which is surrounded by walls 40. The solid product chemistry is placed on a support member 50, which is shown to be a product grate comprising interlocking wires. A liquid, such as water, is connected to dispenser 10 via the liquid inlet 32 on the bottom side of the dispenser 10. The liquid is connected to the button 26 such that pressing the button will pass liquid into the dispenser 10 to come in contact with the product chemistry. The liquid is passed through a liquid source 34 via a fitment splitter 36. As shown, the liquid source is a split, two channel liquid source for different flow paths. Each of the paths contains a flow control (not shown) to properly distribute liquid in the intended amounts. This flow control can be changed to alter the turbulence of the liquid coming in contact with the solid product to adjust the turbulence based on the characteristics to maintain the formed product chemistry within an acceptable range of concentration. For example, the liquid may pass through the liquid source 34 and out of the liquid source nozzle 44. The liquid source nozzle 44 is positioned adjacent a manifold diffuse member 46, which may also be known as a puck member, such that the liquid passing through the liquid nozzle 44 will be passed through manifold diffuse ports of the manifold diffuse member 46.

Furthermore, the invention contemplates that, while positioned on the support member 50, the product chemistry may be fully submerged, partially submerged, or not submerged at all. The submersion level, or lack thereof, can be dependent upon many factors, including but not limited to, the chemistry of the product, the desired concentration, the fluid used to erode the chemistry, frequency of use of the dispenser, along with other factors. For example, for normal use with water as the eroding element, it has been shown that it is preferred to have approximately one-quarter inch of the bottom portion of the product chemistry submerged to aid in controlling the erosion rate of the chemistry. This will provide for a more even erosion of the product as it is used, so that there will be less of a chance of an odd amount of product left that must be discarded or otherwise wasted.

The liquid will continue in a generally upwards orientation to come in contact with a portion or portions of the solid product supported by the product grate 50. The mixing of the liquid and the solid product will erode the solid product, which will dissolve portions of the solid product in the liquid to form a product chemistry. This product chemistry will be collected in the product chemistry collector 56, which is generally a cup-shaped member having upstanding walls and bottom floor comprising the manifold diffuse member 46. The product chemistry will continue to rise in the product chemistry collector 56 until it reaches the level of an overflow port 52, which is determined by the height of the wall comprising the product chemistry collector 56. According to some aspects and/or embodiments, the product chemistry collector 56 is formed by the manifold diffuse member 46 and walls extending upward therefrom. The height of the walls determines the location of the overflow port 52. The product chemistry will escape or pass through the overflow port 52 and into the collection zone 42, in this case a funnel. The liquid source 34 includes a second path, which ends with the diluent nozzle 60. Therefore, more liquid may be added to the product chemistry in the collection zone 42 to further dilute the product chemistry to obtain a product chemistry having a concentration within the acceptable range.

Other components of the dispenser 10 include a splash guard 54 positioned generally around the top of the collection zone 42. The splash guard 54 prevents product chemistry in the collection zone 42 from spilling outside the collection zone 42.

The liquid source 34 includes a second path, which ends with the diluent nozzle. Therefore, more liquid may be added to the product chemistry in the collection zone 42 to further dilute the product chemistry to obtain a product chemistry having a concentration with the acceptable range.

Other components of the dispenser 10 include a splash guard positioned generally around the top of the collection zone 42. The splash guard prevents product chemistry in the collection zone 42 from spilling outside the collect zone 42.

The dispenser 10 may incorporate pressurized air into the system to partially displace water used to dissolve the solid chemical block and produce a higher concentration level in the solution. The use of air allows the system to maintain pressure, which for impingement. The air also maintains the spray area for the solid block, while reducing the amount of water volume required to create a solution. The gas or air is also vented out of the system, and thus does not become part of the final chemistry solution. The use of air also eliminates, or at least minimizes, fowling or plugging of the manifold of perforations.

The use of air and water helps solve the limitations on solution concentration adjustability, without imposing drastic structural figuration changes in the dispenser 10. The present invention introduces air into the water line to displace liquid volume. Air aids in helping the system maintain spray pressure/volume, with the air leaving the system as soon as its erosion work is complete.

The dispenser 10 is wired for electrical power inside the housing 12. The dispenser 10 may include an electrical air or gas pump. Their pump includes a nipple to which an airline (not shown for clarity) is attached. The airline can be single line, or split into multiple lines, for connection to plumbing points or couplers, so as to introduce air into the cavity 38. Thus, liquid, such as water, from the liquid source 34 is combined with gas, such as air, from the pump to effectively dissolve solid chemistry block, and produce to concentrate solution. Upon the activation of the dispenser 10 by pushing the button 26, liquid begins to flow into the system. The pump may be activated simultaneously upon pressing the button 26, or alternatively, a delay circuit for the pump can be utilized to ensure the water path is established before introducing air into the system.

By combining air with liquid to dissolve the solid chemistry block, the solution concentrate can be 2-3 times greater than a turbulent flow dispenser using water alone. Also, the volume of water can be reduced at least 25% due to the addition of air, thus providing costs saving to the operator.

Thus, the combination of an incompressible liquid and a compressible gas to uniformly dissolve or erode the solid chemistry block provides advantages which cannot be achieved without the combination of liquid and gas.

The invention further includes a capsule 110, as best shown in FIGS. 4-9, which contains the solid chemistry product for use in the dispenser 10. The capsule 110 is ideally suited for caustic or other hazardous chemistries which create health risks to users if exposed to the chemistries.

Figure 4:
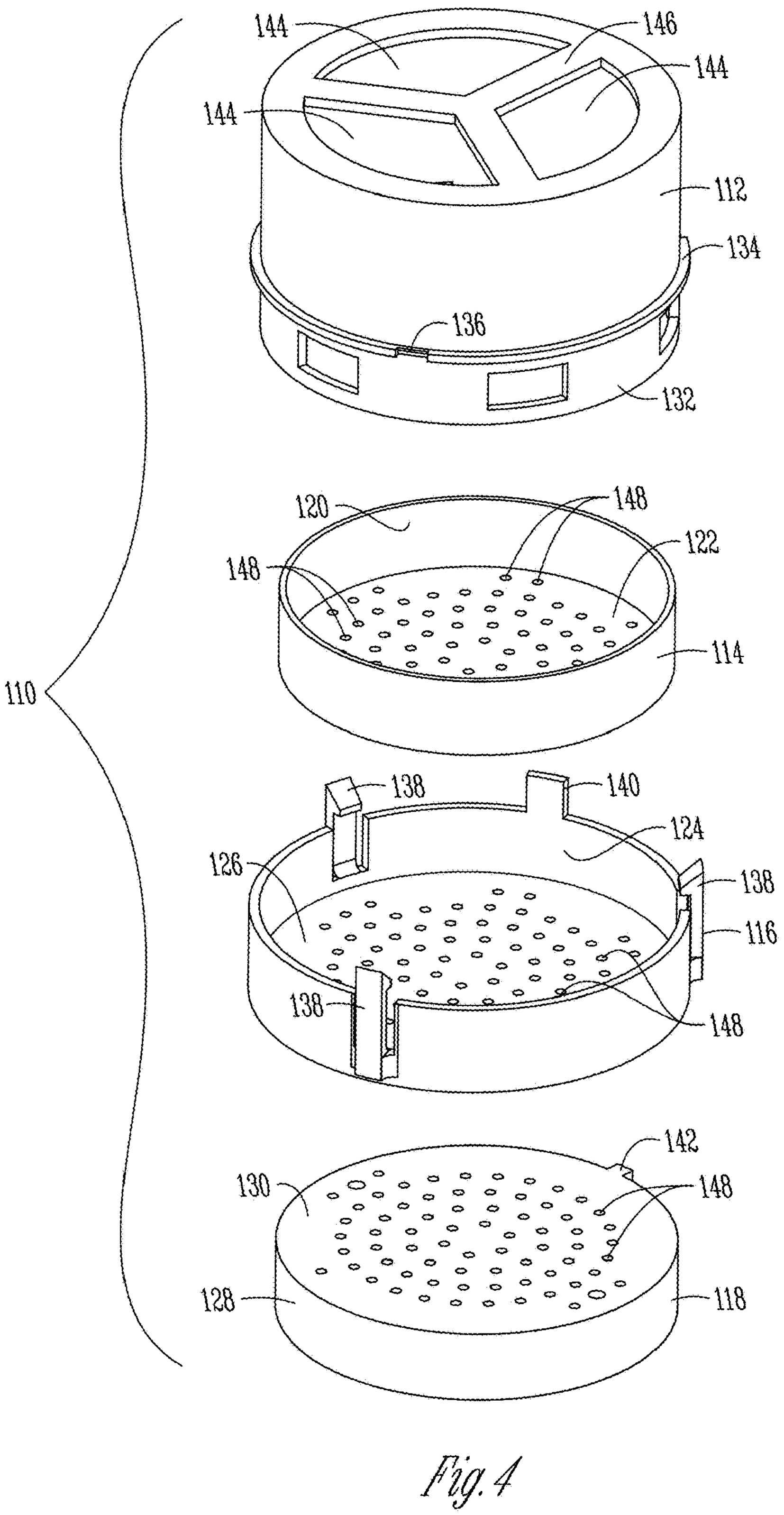
FIG. 4 is an exploded view of the capsule components.

More particularly, the capsule 110 has an overall cylindrical shape and is comprised of three nested components, as best shown in FIGS. 4 and 5. The components include an upper housing 112 which contains the solid product, an intermediate pan 114, and a lower base 116. In the drawings, a shelf 118 is an internal piece of the dispenser 10 which supports the capsule 110. The intermediate pan member 114 has a sidewall 120 and a perforated floor 122. Similarly, the lower base 116 has a sidewall 124 and a perforated floor 126. The shelf 118 has a sidewall 128 with a perforated top 130. As shown in FIG. 5, the wall 120 of the intermediate pan 114 fits within the sidewall 132 of the upper housing 112, and the sidewall 124 of the lower member 116 extends around the sidewall 132 of the upper housing 112. The shelf 118 fits within the sidewall 124 of the second intermediate member 116 to support the capsule 110. Alternatively, the present disclosure contemplates the lower base 116 and shelf 118 may integrally form one solid component. The upper housing 112 and the lower base 116 are rotatable relative to one another between an open position and a closed position. In the open position, the perforations of the floors 122, 126, and 130 are aligned, as shown in FIG. 5 to allow fluid to spray upwardly and dissolve the product. In the closed position, the perforations of the floors 122 and 126 are misaligned to prevent product flow through the perforations.

The upper container 112 includes a perimeter flange 134 having a series of notches 136. The lower base 116 has a plurality of resilient fingers or locking tabs 138 each having an upper hook adapted to retentively engage the perimeter flange 134 of the container 112. The notches 136 allow the hooks of the tabs to pass upwardly there through, without overstressing the tabs during assembly of the upper housing 112 and the lower member 116. The lower member 116 can then be twisted or rotated to lock onto the upper housing 112. Alternatively, the housing 112 and base 116 can be snap fit together via the hooks and perimeter flange. The lower base 116 also has an upstanding locking tab 140. The upper housing 112 has a pair of stops (not shown) spaced apart approximately 30°. The tab 140 resides between the stops, which limit the rotation of the upper housing 112 to substantially 30° in either direction by contact with the tab 140. The shelf 118 has a key 142 extending radially outwardly from the sidewall 128 which is adapted to fit into a slot or recess 143 of the lower base 116, so as to assure proper mating of the capsule 110 into the dispenser 10 while still allowing rotation of the upper housing 112.

The top of the housing 112 has openings 144 with one or more cross members 146 which define a handle. It is understood that the handle may take other shapes in forms, including a foldable handle.

The housing 112 also has a plurality of openings 148 which allow for drainage of the solution formed by dissolution of the chemistry block product in the housing 112 by the fluid during operation of the dispenser.

Figure 5A:
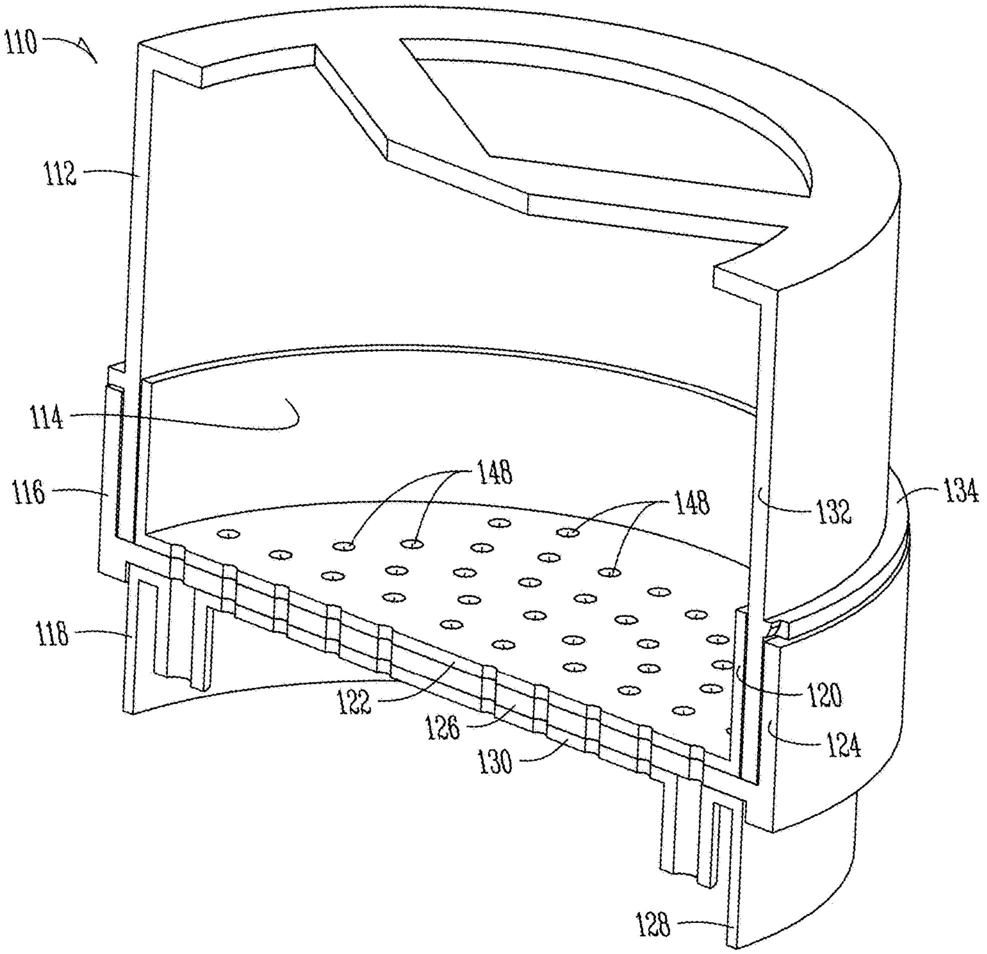
FIG. 5A is a sectional view of the capsule, taken along line 5.5 of FIG. 3.
Figure 5B:
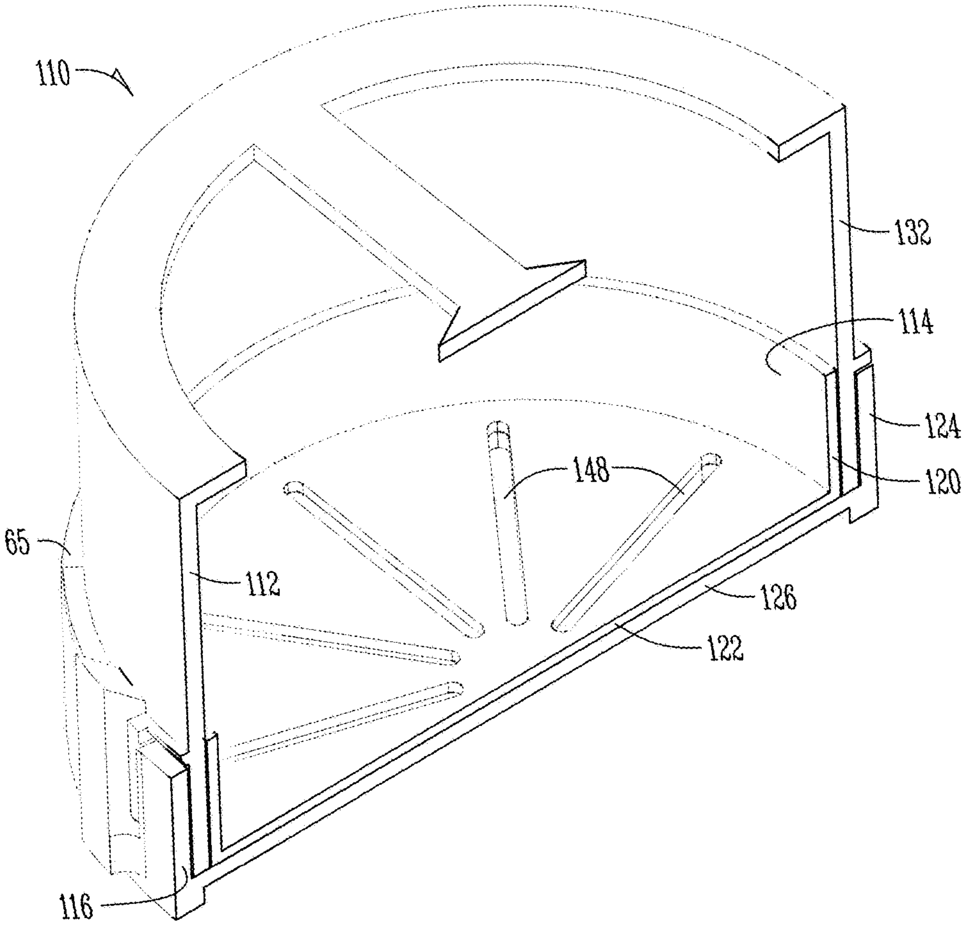
FIG. 5B is a sectional view of an alternative embodiment of the capsule wherein circular holes are substituted for stadium-shaped slots.
Figure 6:
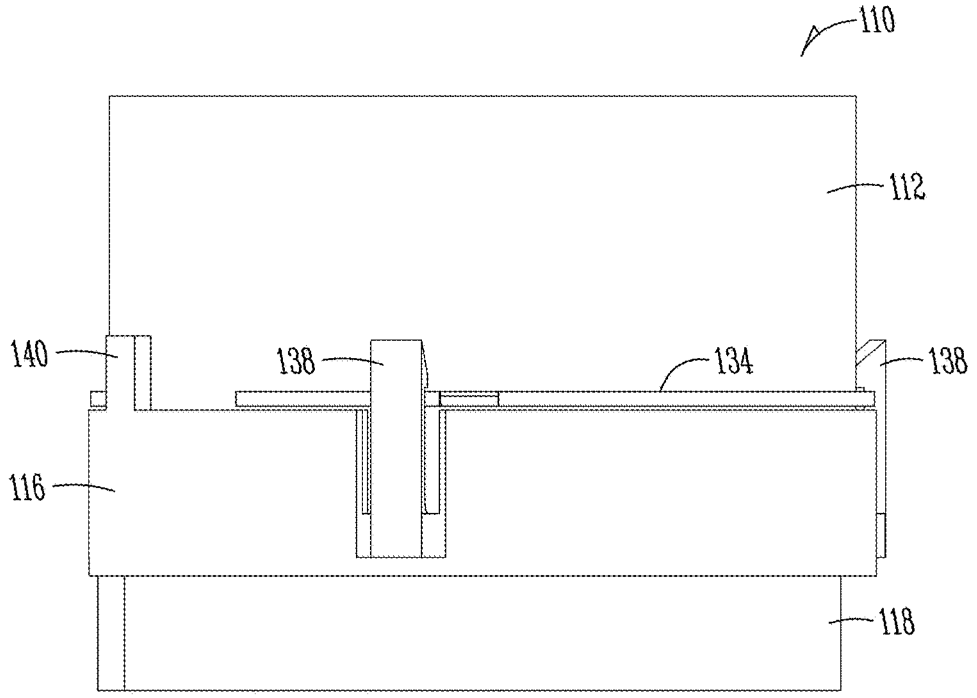
FIG. 6 is a side elevation view of the capsule.
Figure 7:
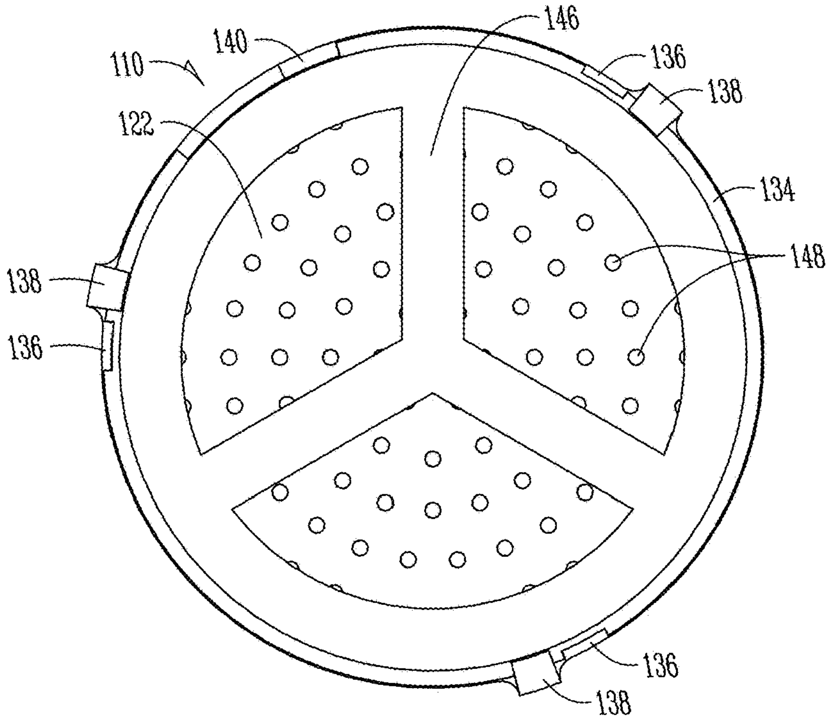
FIG. 7 is a top plan view of the capsule in a closed position for shipping, handling and storage.
Figure 8:
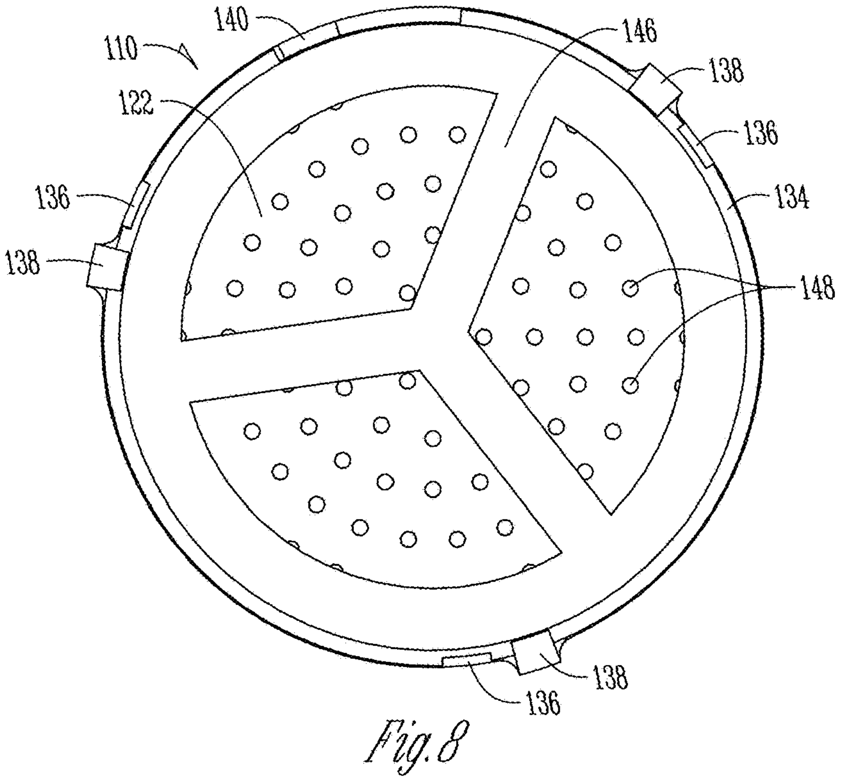
FIG. 8 is a plan view of the capsule in the open position for use in the dispenser.
Figure 9:
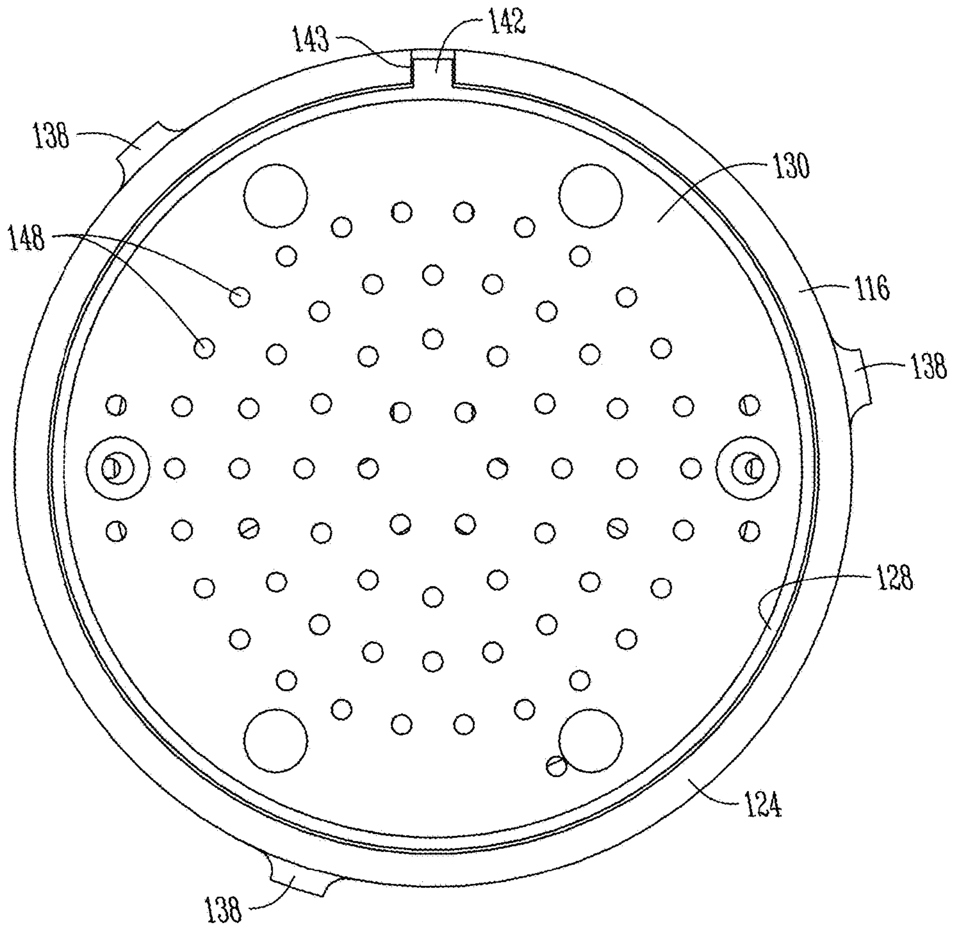
FIG. 9 is a bottom plan view of the capsule.

When the capsule 110 is inverted and loaded into the cavity of the dispenser 10, the perforations 148, such as holes or slots in the floors 122, 126, and 130, are adjacent the water spray component of the dispenser 10. The perforations 148 in the floors 122, 126, 130 may form circles (as shown in FIG. 5A), ovals, stadiums (as shown in FIG. 5B), partial circles (such as semicircles) rectangles, triangles, irregular polygons, cones, any other known shown shapes, or combinations of any of the preceding shapes. When the capsule 110 is installed in the dispenser 10, the key 142 aligns the perforations of the lower member 116 with the perforations of the shelf 118. After the capsule 110 is inserted into the cavity, the upper housing 112 can be turned or rotated by the handle 146 so as to move the capsule 110 from the closed position with the perforations misaligned to the open position with all the perforations aligned. Water can then be sprayed through the openings to dissolve or erode the product in the container 112. Before the capsule 110 is removed from the dispenser 10, the upper housing 112 can be rotated to the closed position, thereby preventing any residual product from escaping and thereby insuring that the user cannot come in new contact with the concentrated chemistry. A lock prevents accidental rotation when the capsule 110 is not in the cavity 38.

Preferably, the solid chemistry product is shrink wrapped before packaging in the container 112. After the capsule 110 is installed in the cavity 38, the shrink wrap plastic will dissolve by exposure to water or other liquid.

The dispenser 10 according to the aspects of the present disclosure may also include components such as an intelligent control and communication components. Examples of such intelligent control units may be tablets, telephones, handheld devices, laptops, user displays, or generally any other computing device capable of allowing input, providing options, and showing output of electronic functions. Input may be provided to the intelligent control unit via input devices such as touch-screen displays, a plurality of knobs, dials, switches, buttons, etc. Still further examples of such intelligent control units include a microprocessor, a microcontroller, or another suitable programmable device) and a memory. The controller also can include other components and can be implemented partially or entirely on a semiconductor (e.g., a field-programmable gate array ("FPGA")) chip, such as a chip developed through a register transfer level ("RTL") design process. The memory includes, in some embodiments, a program storage area and a data storage area. The program storage area and the data storage area can include combinations of different types of memory, such as read-only memory ("ROM", an example of non-volatile memory, meaning it does not lose data when it is not connected to a power source), random access memory ("RAM", an example of volatile memory, meaning it will lose its data when not connected to a power source) Some examples of volatile memory include static RAM ("SRAM"), dynamic RAM ("DRAM"), synchronous DRAM ("SDRAM"), etc. Examples of non-volatile memory include electrically erasable programmable read only memory ("EEPROM"), flash memory, a hard disk, an SD card, etc. In some embodiments, the processing unit, such as a processor, a microprocessor, or a microcontroller, is connected to the memory and executes software instructions that are capable of being stored in a RAM of the memory (e.g., during execution), a ROM of the memory (e.g., on a generally permanent basis), or another non-transitory computer readable medium such as another memory or a disc.

A communications module can be included with the dispenser and can be configured to connect to and communicate with another controller, such as a computer, tablet, server, or other computing device. This could allow the dispenser to provide data or other information (e.g., warnings, status, notices, etc.) associated with the dispenser to a remote location of the additional controller to allow the real-time information and stored information for the dispenser. The information could be used to determine issues, forecast, or otherwise track information related to the dispenser. The communication could also be in the form of inputs such that the communication could include a command to the dispenser from a remote location.

In some embodiments, the dispenser includes a first communications module for communicating with a secondary device (other dispenser or remote controller), and/or a second communications module for communicating with a central location (server, computer, or other master controller). For sake of simplicity, the term "communications module" herein applies to one or more communications modules individually or collectively operable to communicate with both the mobile reader and the central location.

The communications module communicates with the central location through the network. In some embodiments, the network is, by way of example only, a wide area network ("WAN") (e.g., a global positioning system ("GPS"), a TCP/IP based network, a cellular network, such as, for example, a Global System for Mobile Communications ("GSM") network, a General Packet Radio Service ("GPRS") network, a Code Division Multiple Access ("CDMA") network, an Evolution-Data Optimized ("EV-DO") network, an Enhanced Data Rates for GSM Evolution ("EDGE") network, a 3GSM network, a 4GSM network, a Digital Enhanced Cordless Telecommunications ("DECT") network, a Digital AMPS ("IS-136/TDMA") network, or an Integrated Digital Enhanced Network ("iDEN") network, etc.), although other network types are possible and contemplated herein. In certain embodiments, the network is a GSM or other WAM which is operable to allow communication between the communications module and the central location during moments of low-quality connections, such as but not limited to when the cleaning machine is near a window.

The network can be a local area network ("LAN"), a neighborhood area network ("NAN"), a home area network ("HAN"), a metropolitan area network ("MAN"), an enterprise private network ("EPN"), a virtual private network ("VPN"), or a personal area network ("PAN") employing any of a variety of communications protocols, such as Wi-Fi, Bluetooth, ZigBee, near field communication ("NFC"), TCP-based protocol (Transmission Control Protocol), UDP-based protocol (User Datagram Protocol), etc., although other types of networks are possible and are contemplated herein. Communications through the network by the communications module or the controller can be protected using one or more encryption techniques, such as those techniques provided in the IEEE 802.1 standard for port-based network security, pre-shared key, Extensible Authentication Protocol ("EAP"), Wired Equivalency Privacy ("WEP"), Temporal Key Integrity Protocol ("TKIP"), Wi-Fi Protected Access ("WPA"), and the like.

The connections between the communications module and the network are wireless to enable freedom of movement and operation of the mobile cleaning machine without being physically tethered to a computer or other external processing device to facilitate such communications. Although such a modality of communications is preferred for at least this reason, it is contemplated that the connections between the communications module and the network can instead be a wired connection (e.g., a docking station for the communications module, a communications cable releasably connecting the communications module and a computer or other external processing device, or other communications interface hardware), or a combination of wireless and wired connections. Similarly, the connections between the controller and the network or the network communications module are wired connections, wireless connections, or a combination of wireless and wired connections in any of the forms just described. In some embodiments, the controller or communications module includes one or more communications ports (e.g., Ethernet, serial advanced technology attachment ("SATA"), universal serial bus ("USB"), integrated drive electronics ("IDE"), etc.) for transferring, receiving, or storing data.

The communications module can be powered by a dedicated power source, such as a battery, battery pack, or wired power (e.g., AC power socket or other power source). In some aspects of the invention, the communications module can be powered by the same power supply as that of the dispenser, such as by battery or by wired power. Still further, it is contemplated that the communications module can be powered wirelessly or by power over ethernet.

The central location can include a centrally located computer, a network of computers, or one or more centrally located servers. The central location can be adapted to store, interpret, and communicate data from one or more dispensers 10, and can also interpret the data and communicate the interpreted data to a user.

The foregoing description has been presented for purposes of illustration and description and is not intended to be an exhaustive list or to limit the invention to the precise forms disclosed. It is contemplated that other alternative processes and structures obvious to those skilled in the art are to be considered in the invention.

From the foregoing, it can be seen that the present invention accomplishes at least all of the state of objectives.

LIST OF REFERENCE NUMERALS

The following reference numerals are provided to facilitate an understanding and examination of the present disclosure and are not an exhaustive list. Provided it is possible to do so, elements identified by a numeral may be replaced or used in combination with any elements identified by a separate numeral. Additionally, numerals are not limited to the descriptors provided herein and include equivalent structures and other objects possessing the same function.

10 dispenser
12 housing
14 front door
16 handle
18 window
20 hinge
22 front fascia
24 product ID window
26 button
28 rear enclosure
30 mounting plate
32 liquid inlet
34 liquid source
36 fitment splitter
38 cavity
40 walls
42 collection zone
44 liquid source nozzle
46 manifold diffuse member
50 support member
52 overflow port
54 splash guard
56 product chemistry collector
58 outlet
60 diluent nozzle
62 backflow prevention device
110 capsule
112 upper housing
114 intermediate pan member
116 lower base
118 shelf
120 sidewall
122 perforated floor
124 sidewall
126 perforated floor
128 sidewall
130 perforated top
132 sidewall
134 perimeter flange
136 notches
138 resilient fingers or locking tabs
140 upstanding locking tab
142 key
143 slot or recess
144 openings
146 cross members
148 perforations, such as holes or slots The disclosure is not to be limited to the particular embodiments described herein. The previous detailed description is of a small number of embodiments for implementing the disclosure and is not intended to be limiting in scope. The following claims set forth a number of the embodiments of the disclosure with greater particularity.

What is claimed is:

1. A capsule for storing caustic solid product to be dissolved and dispensed by a turbulent flow dispenser, comprising:

an upper housing and a lower base coupled together to form a chamber for holding the caustic solid product;

a pan inside the chamber; the pan having perforations;

the lower base having perforations;

the upper housing and lower base being rotatable relative to one another between a closed position wherein the perforations of the pan are misaligned with the perforations of the lower base and an open position wherein the perforations of the pan are aligned with the perforations of the lower base; and the coupled upper housing and lower base being configured to fit inside a cavity in the dispenser wherein the product is dissolved to produce a solution;

wherein one of the upper housing and lower base has a lock button to prevent inadvertent rotation to the open positions.

2. The capsule of claim 1, wherein the upper housing and lower base are coupled to form a cylindrical body.

3. The capsule of claim 2, wherein the cylindrical body has a longitudinal axis, and rotation between the open and closed positions is about the longitudinal axis.

4. The capsule of claim 1, wherein the upper housing and lower base are twist locked together.

5. The capsule of claim 1, wherein one of the upper housing and lower base has a perimeter flange and the other of the upper housing and lower base has resilient fingers to releasably engage the flange so as to secure the upper housing and lower base together.

6. The capsule of claim 1, wherein one of the upper housing and lower base includes a key slot to mating receive a key tab in the dispenser to orient the housings in the cavity.

7. A turbulent flow dispenser for producing a solution from a solid chemistry product, comprising:

a housing with a cavity therein and a perforated shelf in the cavity;

a cylindrical capsule configured to fit into the cavity and containing the solid chemistry product;

the cylindrical capsule including upper and lower members which are rotatable about a longitudinal axis of the cylindrical capsule and relative to one another between open and closed positions;

the cylindrical capsule having perforations which align with the shelf perforations when the cylindrical capsule is in the open position and which are offset from the shelf perforations when the cylindrical capsule is in the closed position; and a fluid conduit for introducing fluid into the cavity when the cylindrical capsule is in the open position.

8. The turbulent flow dispenser of claim 7, wherein the upper and lower members are separable for loading the solid chemistry product into the cylindrical capsule.

9. The turbulent flow dispenser of claim 7, wherein the shelf supports the cylindrical capsule in the cavity.

10. The turbulent flow dispenser of claim 7, wherein the shelf and lower member are keyed together in the cavity to allow rotation of the upper member relative to the lower member.

11. A method for obtaining a product chemistry from a hazardous solid product, comprising:

providing a sealed capsule containing the hazardous solid product;

installing the sealed capsule into a cavity in a turbulent flow dispenser;

rotating a portion of the capsule to open perforations in the capsule;

introducing fluid through the capsule perforations to erode the solid product and produce a solution from the solid product and the fluid; and locking the rotatable portion of the capsule against accidental rotation.

12. The method of claim 11 wherein the capsule has an upper housing and a lower base which are rotatable relative to one another, and the rotation step rotates one of the upper and lower portions.

13. The method of claim 12 wherein the upper housing and lower base are nested in a co-axial configuration, and the rotation is about a longitudinal axis of the nested portions.

14. The method of claim 11, wherein the rotation step occurs after the capsule is installed in the cavity.

15. The method of claim 11 wherein the rotation step occurs before the capsule is installed in the cavity.

16. The method of claim 11, wherein the perforations are beneath the solid product in the capsule.

17. The method of claim 11, wherein the capsule is cylindrical, and the rotation is about a longitudinal axis of the capsule.

18. The method of claim 11, wherein an operator handles the capsule without exposure to the hazardous solid product.

* * * * *